Figure 1:
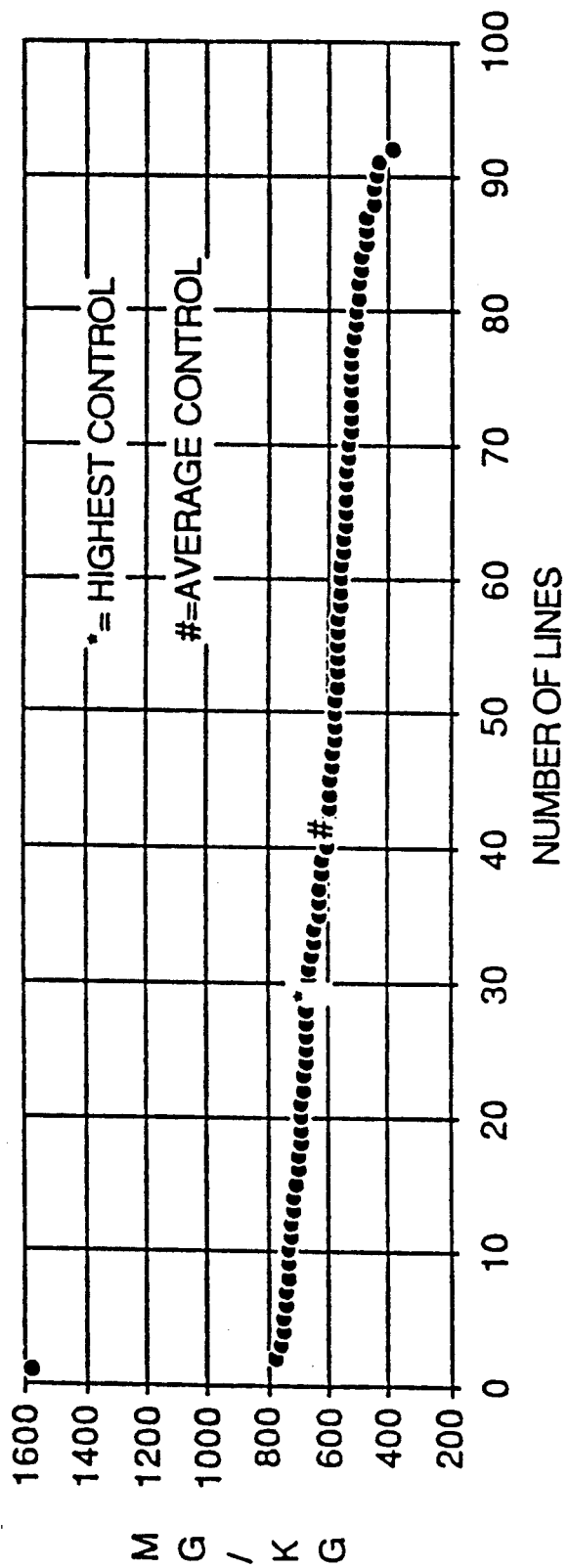

United States Patent [19]

Whitaker

[11] Patent Number: 5,012,040
[45] Date of Patent: Apr. 30, 1991

[54] SOMACLONAL VARIANTS OF NICOTIANA GLUTINOSA

[75] Inventor: Robert J. Whitaker, Burlington, N.J.

[73] Assignees: DNA Plant Technology Corporation, Cinnaminson, N.J.; Firmenich SA, Geneva, Switzerland

[21] Appl. No.: 256,515

[22] Filed: Oct. 12, 1988

[51] Int. Cl.$^5$ .............................................. A01H 5/00
[52] U.S. Cl. .................................. 800/200; 800/230; 800/DIG. 40; 47/58
[58] Field of Search ........... 800/1, 200, 230, DIG. 40; 47/58; 568/819

[56] References Cited
PUBLICATIONS

Bailey et al. (1974) J. Gen. Microbiol. 85, Pt. 1, pp. 57-64, abstract cited.
Whitaker et al. (1986) in Evans et al., eds., Handbook of Plant Cell Culture, vol. 4, Macmillan Publ. Co., NY, pp. 264-286.
Marsalek L. (1984) Acta Universitatis Agriculturae Brno, A (Facultas Argonomica) 32(2): 13-24, abstract cited.

*Primary Examiner*—Elizabeth C. Weimar
*Assistant Examiner*—Gary Benzion
*Attorney, Agent, or Firm*—Pennie & Edmonds

[57] ABSTRACT

The present invention relates to novel plants of the species *Nicotiana glutinosa,* which produce unusually high levels of sclareol.

12 Claims, 2 Drawing Sheets

SOMACLONAL VARIANTS OF NICOTIANA GLUTINOSA

TABLE OF CONTENTS

1. Introduction
2. Background of the Invention
3. Summary of the Invention
4. Brief Description of the Figures
5. Detailed Description of the Invention
   5.1. Obtaining Somaclonal Variants

1. INTRODUCTION

The present invention relates to novel plants producing unusually high levels of sclareol. More specifically, the invention relates to somaclonal variants of *Nicotiana glutinosa* which exhibit a several-fold increase in the production of sclareol relative to the naturally occurring plant. The availability of these novel plant lines produces a convenient, reliable source of sclareol, which can be produced in commercial quantities.

2. BACKGROUND OF THE INVENTION

The labdane diterpene sclareol (labd-14-ene8,13-diol) is a compound of substantial value to the fragrance industry. Sclareol and related derivatives are noted as starting materials in perfume manufacture, and also to enhance the flavor of tobacco (U.S. Pat. No. 4,441,514). The compound is found in nature in many plant sources, among these including *Acacia sp.* (Fonster et al., *Phytochemistry* 24:2991–1993, 1985), *Salvia palestina Phytochemistry* 24:1386–1387, 1985) *Stevia monardaefolia* (*Phytochemistry* 21:2369–1371, 1982), *Nicotiana glutinosa* (Bailey et al. *J. Gen. Microbiol.* 85:57–84, 1974), and *Salvia sclarea* (U.S. Pat. No. 3,060,172). The latter species, also known as clary sage, represents the primary commercial source of sclareol at the present time. The sclareol produced by *S. sclarea* occurs in the flower stalks in the epidermal appendages or hairs known as trichomes. Although the concentration of sclareol in these hairs is relatively high, this is the only location on the plant where sclareol is produced; there is little or no sclareol present in the leaf, root or stems of clary sage. Thus, the quantities of sclareol that can be derived from this plant are relatively limited. To further complicate matters, clary sage flower stalks are sensitive to rain, so that, under routine environmental conditions, the normal yield of sclareol may be even further reduced.

An alternate source of sclareol would clearly be desirable, but to date none of the other known botanic producers of sclareol has been found to be a suitable substitute for clary sage. It has recently been discovered, however, that *Nicotiana glutinosa* produces sclareol in leaves, stems and flower stalks. *N. glutinosa* has never been produced in commercial quantities, however and the overall amounts produced are still relatively small. Nonetheless, the extensive distribution of sclareol in the plant and its relative hardiness makes *N. glutinosa* a valuable candidate for replacement and/or supplement of clary sage, if sclareol production could be increased. One possible means by which this could possibly be achieved is somaclonal variation.

SOMACLONAL VARIATION

Methods of plant tissue culture have now been used for years as a means of asexual reproduction, enabling a more rapid rate of propagation than is available with traditional vegetative propagation. It is of course expected that the regenerated plants will be exact copies of the plant from which the tissue explant was taken. Early in the history of plant tissue culture, it was noticed that phenotypic variants commonly occurred among regenerated plants. These anomalies were typically dismissed as artifacts of tissue culture, representing "epigenetic" events which were of no value scientifically, except as a curiosity.

It has been more recently recognized that the appearance of such variants is a relatively regular occurrence in certain plants, and this provides a potentially valuable source of genetic variability for use in crop improvement (Larkin and Scowcroft, *Theor. Appl. Genet* 60:197–214, 1981; Evans et al., *Amer. J. Bot.* 71:759–774, 1984). The resulting variants are now referred to as somaclonal variants or somaclones and have been observed in a number of different plant species, including tobacco.

A number of different techniques have been used to induce or favor the production of somaclonal variants (Reisch, "Genetic Viability in Regenerated Plants", in *Handbook of Plant Cell Culture,* Vol. 1, Chap. 25, 1983, McMillan Publishing). Among the manipulations which may be used to encourage variation are long-term culture cycles, protoplast culture cycles, callus culture cycles, explants from specific tissue types, growth on a specific nutrient medium or hormone formulation, or the use of specific genotypes known to produce increased amounts of variations. These techniques are not mutually exclusive, and one or more may be combined to achieve the desired level of variation.

The techniques described above have not proven to be unusually applicable to all plants, however. Some species may readily produce somaclonal variants in, for example, a protoplast culture cycle, while other species, even within the same genus, will not. Similarly, there is no way to predict, *a priori,* the nature of the somaclones which will be produced, until the conditions which induce variation for a particular species have been determined. In essence, unless the species in question has previously been shown to produce somaclones, with any degree of certainty, it is impossible to know whether somaclones will be produced, and for what type of characteristics variation will be observed.

SOMACLONAL VARIATION IN NICOTANA

Isolation of *in vitro* mutants from cultured *Nicotiana sp.* has been reported by many workers (See, Flick and Evans, "Tobacco" in *Handbook of Plant Cell Culture;* Vol. 2, Chap. 21, Table 5, 1984; Barlier and Dulieri *Ann. Amelior. Plant.* 30:321–344, 1980. Most of these mutants have been isolated from *N. tabacum,* cultivated tobacco. The majority of those reported have been specifically selected for resistance to an antimetabolite, such as antibiotics, fungicides and herbicides. Other wild species of *Nicotiana,* specifically *N. sylvestris* and *N. plumbaginifolia* have also been shown to produce mutants *in vitro.* However there has not previously been any demonstration, or indeed any attempt, to produce somaclones from *N. glutinosa.*

The present invention has now identified a means for producing somaclonal variants, and regenerated plants therefrom, in the species *Nicotiana glutinosa;* more importantly, however, among the somaclonal variants produced are a number of lines which produce much higher than average levels of sclareol. Lines such as these have been repeatedly and reliably obtained from an *N. glutinosa* somaclonal variation program, and thus represent a novel and valuable source for the production of commercial quantities of sclareol.

3. SUMMARY OF THE INVENTION

The present invention provides novel lines of the species *Nicotiana glutinosa* which produce unusually high levels of the labdane diterpene sclareol. Specifically, these novel lines produce at least about 800 mg sclareol/kg of fresh plant material and typically at least about 1000 mg/kg or more of plant material. This represents at least up to a 2- to 3-fold increase in sclareol production over unmodified *N. glutinosa*, which normally yields a maximum of about 300-600 mg/kg. The use of these improved *N. glutinosa* lines also provides an advantage over the traditional method of obtaining sclareol from clary sage. Although clary sage can produce large quantities of sclareol, the level of production tends to be extremely variable. For example, yield for clary sage can be anywhere from 2-31 kg/acre. This compares with 7-10 kg/acre for unmodified *N. glutinosa* somaclones. Also, clary sage requires a growing period of about 18 months before sclareol can be obtained in significant quantities. Therefore, the present somaclone lines provide a more reliable and convenient source of sclareol than traditional sources.

These lines also provide the basis for the production of hybrid lines, utilizing as one or both parents, the novel lines of the present invention. Also within the scope of the present invention are clones, somaclones, gametoclones and mutants of the novel lines.

The invention also provides a method of producing *Nicotiana* lines having above average labdane content which comprises culturing an explant of young tissue of *Nicotiana* on a nutrient medium containing at least one cytokinin at a concentration of about 5-20 μM for a period of time sufficient to obtain a callus; regenerating plants from said callus; and screening the regenerated plants for variants producing higher than average levels of sclareol.

4. BRIEF DESCRIPTION OF THE FIGURES

FIG. 1 presents a summary of the pattern of sclareol production in somaclones of the DE line of *Nicotiana glutinosa*.

Figure 2:
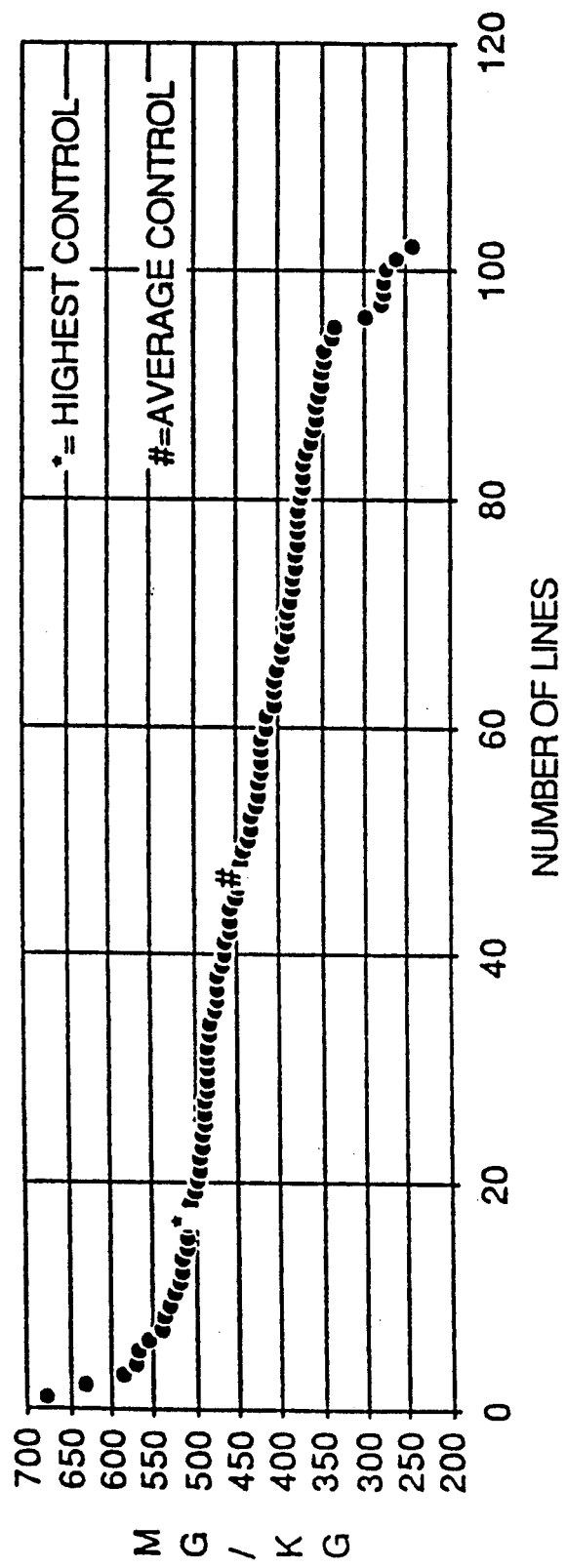

FIG. 2 presents a summary of the pattern of sclareol production in somaclones of the VS line of *Nicotiana glutinosa*.

5. DETAILED DESCRIPTION OF THE INVENTION

5.1. OBTAINING SOMACLONAL VARIANTS

As noted above, somaclonal variation can be induced by placing a tissue explant into an appropriate growth medium. In the present case, the tissue is preferably derived from any young tissue of the plant, particularly young leaf tissue. By "young" in the present context is meant tissue from a preflowering plant. Sterilization of the selected tissue is usually performed prior to culture to prevent growth of contaminated microorganisms. Tissue may be immersed in a dilute solution of sodium hypochlorite (e.g. Clorox) for about ten minutes and there rinsed two or three times with sterile distilled water. Other methods of sterilization will also be recognized by those skilled in the art.

A number of nutrient media suitable for plant tissue culture, each containing a distinctive composition of carbon source, salts, minerals and vitamins, are known in the art. Among those which are suitable as the basal medium are B5 (Gamborg *et al., Exp. Cell Res.* 50:151-158, 1968), White's (White, *A Handbook of Plant and Animal Tissue Culture,* Jaques Cattel Press, Lancaster, PA, 1963) and SH (Schenk and Hildebrandt, *Can. J. Bot.* 56:166-204, 1962). Preferred for the culture procedure, however, is MS medium (Murashige and Skoog, *Physiol. Plant.* 15:473-497, 1962).

Variation in the regenerated plants is induced by the presence of a particular hormonal composition in the medium. It has been discovered that the presence of a relatively high concentration of at least one cytokinin will be effective in inducing variation. Among known cytokinins are 6-benzyladenine (6-BA), zeatin, kinetin, and 2-isopentyladenine (2-iP). Concentrations of at least about 5 μM of cytokinin are effective in producing variants among regenerated plants; however, the quantity and quality of variants obtained appear to vary with the cytokinin concentration. Variation occurs at a low frequency at concentrations of 5 μM, and increases with increasing cytokinin concentration. At cytokinin concentrations of 20 μM or more, while frequency of variation is high, the variations observed tend to be detrimental or undesirable. Therefore, the preferred concentration for the production of high sclareol-producing lines is about 5 μM-20 μM, with the most preferred concentration being about 10 μM. The preferred cytokinin is 6-BA.

Although not necessary for induction of variation, it may also be desirable to include an auxin in the growth medium. Variation will occur in a medium containing only effective amounts of a cytokinin, but the quality of regenerated plants is greatly improved by growth on an auxin- and cytokinin-containing medium. Auxins useful in the present method include indole acetic acid (IAA), indole butyric acid (IBA), naphthalene acetic acid (NAA), and 2,4-dichlorophenoxyacetic acid (2,4-D), with IAA being preferred. The presence of an auxin, and particularly IAA, tends to promote shoot formation; this limits the period of undifferentiated growth, and may therefore obviate the problem associated with accumulation of or many undesirable mutations in plantlet progency. Generally, a concentration of about 1 μM to about 20 μM of auxin is sufficient to ensure a desirable level of plantlet regeneration.

To initiate regeneration, an explant usually no more than a few square centimeters, is excised from the donor plant and placed on a basal medium with an appropriate hormonal concentration. A callus mass, i.e., a mass of undifferentiated tissue, appears at the cut edges in about 5-10 days; within 2-3 weeks, shoots will begin to appear.

Following shoot regeneration, it is usually preferred to transfer the regenerated shoots to a rooting medium. A preferred rooting medium contains one-half strength MS and naphthalene acetic acid (NAA); the use of NAA increases the frequency of successfully rooted plants. When employed, the preferred concentration for NAA is about 2 μM; however, possible variations in the composition of the rooting medium will be apparent to those skilled in the art. Once regenerated plants have been rooted, they are transferred to pots and grown to maturity.

Because the variant regenerated plants which contain higher levels of sclareol do not differ phenotypically from normal regenerated plants, the screening for the desired variants must be performed chemically on the regenerated plants. Labdanes are extractable from leaves of the plants with methanol. Once active leaves from each plant are collected, weighed, and extracted, the methanol extracts are dried down, and the labdane fraction obtained by solid phase extraction. Gas chromatography is conveniently performed according to the method of R. F. Severson et al. (J. Ag. Food Chem. 38:566) with the minor modifications noted in Example 1, infra. Peak identification can be accomplished by comparison with authentic labdane standards. The concentration of sclareol is determined for each somaclone line, and then compared with the concentrations observed in the highest producing non-variant control lines. As noted above, the range of sclareol yield for average, non-somaclone N. glutinosa lines is about 300–600 mg/kg. Any line producing 800 or more mg sclareol/kg is considered a variant.

In the present trials, leaf explants from two different genotypes of N. glutinosa (designated VS and DE) were cultured and screened for somaclones producing high levels of sclareol. In one line, DE, twenty-six somaclone lines, out of a total of 94, exhibited ranges of sclareol production which were 11–32% over the highest control (see FIG. 1). One line, however, showed a 2.5-fold increase in sclareol (1581 mg/kg) over the highest control. This line, DE-72, also produced 415 mg/kg manool, another labdane; this is approximately a two-fold increase over the highest control. On the other hand, phytol, a non-labdane-alcohol produced by the degradation of chlorophyll was present in amounts similar to those in the controls, indicating that the biochemical and genetic changes that distinguish line 72 involve only the labdane pathway. This is consistent with previous observations on the utility of somaclonal variation for introducing single gene changes into the genome that might regulate an entire biochemical pathway.

Observations on the VS somaclones parallel those seen with DE, with one difference: this genotype is, overall, not as productive as DE for sclareol synthesis, and therefore, VS somaclones do not accumulate sclareol to the level that the DE somaclones do. However, it is worthy of note that a very similar distribution for increased sclareol synthesis (shown in FIG. 2) exists in the VS somaclones when compared to the DE somaclones. Thus, the technique provides a reliable means of obtaining increased labdane production in any given Nicotiana line, and truly outstanding results are obtainable when the starting material is a line already exhibiting sclareol production at the high end of the normal range, i.e., at least about 500–600 mg/kg.

It will be recognized by those skilled in the art that the figures given from average sclareol production by the modified lines of the present invention, and the control line as well, refer to production observed under substantially ideal growing conditions for Nicotiana glutinosa, in one season's production. Clearly, environmental conditions have the potential of affecting overall yield of the plant, as well as production of sclareol itself. It is within the skill of the experienced artisan to design a planting strategy which will optimize yield of sclareol under the environmental conditions of the region where the plants are to be grown. Generally, however, traditional tobacco agronomy is applicable to growth of N. glutinosa. It has been determined that optimum sclareol synthesis occurs at the onset of flowering, and that almost 70% of sclareol production occurs in the top two thirds of the plant. Therefore, by harvesting the top two thirds of the plants after flowering has occurred, optimal sclareol levels can be obtained, and enough plant material will be left in the ground to ensure good secondary growth that will permit a second harvest from the same plot of land. All yield/acre figures presented herein represent the results of two harvests.

The present method has been used to repeatedly produce high labdane-producing lines of Nicotiana glutinosa. Seed of a particularly high sclareol producing line has been deposited with the American Type Culture Collection, under Accession Number 40463. The scope of the present invention is not limited, however, solely to the somaclonal variant lines per se, nor to a single deposited line. The present invention also encompasses all hybrids, both inter- and intraspecific, mutants, somaclones, and gametoclones, derived from the original somaclonal variants, which retain the identifying characteristic of high sclareol production.

The availability of such Nicotiana glutinosa variants provides a novel method by which sclareol may be produced on a commercial scale. Although the production of sclareol by Nicotiana glutinosa has previously been known, this plant has never been exploited for this purpose, presumably because the natural yield of this plant is quite low. The present availability of high-yielding somaclones, however, has now provided a means by which sclareol can be produced in commercially feasible quantities. Thus, the present somaclones represent an improvement in methods for obtaining sclareol from plant sources, by extraction of sclareol from leaves and other plant parts of the novel somaclones of N. glutinosa, having a sclareol content of at least 800 mg/kg of fresh plant weight.

The following non-limiting examples will more clearly illustrate the plant lines and methods of the present invention.

EXAMPLE 1

The following example illustrates conditions under which somaclonal variants of Nicotiana sp. producing higher than normal amounts of labdanes have been repeatedly produced:

Young, fully expanded leaves of Nicotiana glutinosa are isolated from donor plants and surface sterilized. Sterilization for greenhouse grown plants is usually conducted for about 6 minutes in 8% commercial bleach (0.42% sodium hypochlorite). The bleach is rinsed off in three changes of sterile distilled water.

The leaf is cut into 1–5 cm$^2$ sections, and transferred aseptically to a jar containing solid MS medium (Murashige and Skoog, Physiol. Plant. 15:473–479, 1962) with the addition of 6-BA at a concentration of about 10 $\mu$M, and IAA at a concentration of about 10 $\mu$M. A callus mass develops in about 5–10 days, and shoots are regenerated in 2–3 weeks. All shoots regenerated from callus are transferred to a rooting medium comprising MS medium with 2 $\mu$M NAA. Plantlets are recovered on rooting medium from 8–10 weeks after culture initiation. Between 2–10 plants are typically obtained from each explant that regenerated shoots.

Regenerated plants ($R_o$) are placed in soil and transferred to a greenhouse. The $R_o$ plants are self-fertilized, and seed are collected from each regenerated plant to evaluate the next ($R_l$) generation. Seeds for $R_l$ plants were sown in the greenhouse and were transplanted to the replicated field plots to evaluate genetic variability.

EXAMPLE 2

The following procedures illustrate the method of testing for sclareol content in leaves of $R_1$ lines.

Methanol extraction is preferably performed on leaves from the top third of the plant. The leaves are randomized, and then several leaf disks are generated therefrom with a 1.5 cm cork borer, excluding the midvein of the leaf. 10 grams of leaf disks are weighed out and placed in a 250 ml beaker or extraction flask. 100 ml of reagent grade methanol is added to each flask and shaker on a rotary shaker for 8-10 hours at 160 rpm. The solvent is decanted and saved. A fresh 100 ml aliquot of methanol is then added, and shaken for 2 hours. The solvent is decanted and combined with the first reserved solvent fractions.

Drying down of methanol can be achieved in a number of different ways. In a situation in which large numbers of samples are being prepared, drying time can be accomplished by evaporation in a laminar flow hood for 1-2 days. When a small number of samples are being evaluated, the methanol can be evaporated by bubbling nitrogen gas through the methanol for 2-3 hours.

After drying, the residue is dissolved in two 5 ml aliquots of hexane:methylene chloride (1:1), and adding 2.0 ml distilled water to the second 5 ml aliquot to dissolve the water soluble components of the residue. In a 15 ml conical centrifuge tube, 0.5 ml of a 5 mg/ml solution of 1-heptadecanol (internal standard) is combined with the dissolved residue, and the phases allowed to separate. If necessary the volume can be brought up to 10 ml with additional hexane:methylene chloride.

A solid phase extraction column (silica gel, 500 mg adsorbant, 3 ml capacity) is set up and conditioned with 2 ml hexane:methylene chloride. From the top phase of the sample, 1 ml is removed and loaded onto the column. The sample is washed onto the column with 2 ml of hexane:methylene chloride. The column is eluted with 4×0.5 ml aliquots of acetone, and the eluate collected in 0.5 dram vials. The eluant is evaporated with nitrogen gas, and the residue redissolved with 1 ml ethyl acetate. The sample is then read for injection into a gas chromatograph.

Chromatography is conducted according to the method of Severson et al., supra, with the following modifications:

| | |
|---|---|
| Split ratio | 200:1 |
| Column | 25M × .22 mm ID CP-SIL 5CB (CHROMOPAK) |
| Temperature program | 160° C. isothermal (9 minutes) 5° C./minute to 295° C., and hold for 4 minutes |
| Run time | 40 minutes |
| Injection | 1 μl |
| Additional specifications include: | |
| He | 30 ml/min |
| $H_2$ | 30 ml/min |
| Air | 400 ml/min |
| Column Flow | 0.99 ml/min |
| Injection Temperature | 250° C. |
| Detection Temperature | 300° C. |

In this manner, over 200 regenerated plants from each of the VS and DE lines were tested for amount of sclareol production. The results are presented in FIGS. 1 and 2.

What is claimed is:

1. A somaclonal variant *Nicotiana glutinosa* plant which produces at least about 800 mg of sclareol per kg of fresh plant weight and derivatives thereof which produce at least about 800 mg of sclareol per kg of fresh plant weight.

2. The plant of claim 1 which produces at least about 1,000 mg/kg of sclareol and derivatives thereof which produce at least about 1,000 mg/kg of sclareol.

3. The plant of claim 1 which produces at least about 1400 mg/kg of sclareol and derivatives thereof which produce at least about 1400 mg/kg of sclareol.

4. A somaclonal variant *Nicotiana glutinosa* plant which is derived from seed deposited with the American Type Culture Collection under accession number ATCC 40463 and derivatives thereof which produce at least about 800 mg of sclareol per kg of fresh plant weight.

5. Seed of the plant of claim 1.
6. Seed of the plant of claim 2.
7. Seed of the plant of claim 3.
8. Seed of *Nicotiana glutinosa* variant deposited with the American Type Culture Collection under accession number ATCC 40463.
9. A leaf of the plant of claim 1.
10. A leaf of the plant of claim 2.
11. A leaf of the plant of claim 3.
12. A leaf of the plant of claim 4.

* * * * *